United States Patent
Bakshandeh

(10) Patent No.: US 12,318,276 B2
(45) Date of Patent: Jun. 3, 2025

(54) DEVICE FOR DELIVERING SILICONE PROSTHESIS INTO A SURGICAL POCKET

(71) Applicant: Norman Bakshandeh, Manhasset, NY (US)

(72) Inventor: Norman Bakshandeh, Manhasset, NY (US)

( * ) Notice: Subject to any disclaimer, the term of this patent is extended or adjusted under 35 U.S.C. 154(b) by 692 days.

(21) Appl. No.: 17/738,124

(22) Filed: May 6, 2022

(65) Prior Publication Data
US 2023/0355370 A1    Nov. 9, 2023

(51) Int. Cl.
A61F 2/12 (2006.01)
A61F 2/00 (2006.01)

(52) U.S. Cl.
CPC .............. *A61F 2/0095* (2013.01); *A61F 2/12* (2013.01)

(58) Field of Classification Search
CPC .. A61F 2/0095; A61F 2/12; A61F 2220/0058; A61F 2250/0018; A61F 2250/0091
See application file for complete search history.

(56) References Cited

U.S. PATENT DOCUMENTS

| | | | |
|---|---|---|---|
| 5,052,554 A | 10/1991 | Leonard | |
| 7,267,885 B1 | 9/2007 | Woo et al. | |
| 8,211,173 B2 | 7/2012 | Keller et al. | |
| 10,092,385 B2 * | 10/2018 | Anderson | A61F 2/0095 |
| 10,722,335 B1 * | 7/2020 | Rosenberg | A61F 2/12 |
| 10,939,985 B2 * | 3/2021 | Winn | A61F 2/0095 |
| 11,058,530 B2 * | 7/2021 | Chen | A61L 27/502 |
| 11,135,051 B2 * | 10/2021 | Bakshandeh | A61F 2/0095 |
| 11,324,581 B2 * | 5/2022 | Heneveld | A61F 2/0095 |
| 11,350,917 B2 * | 6/2022 | Barbot | A61F 2/12 |
| 11,583,382 B2 * | 2/2023 | Harvie | A61F 2/12 |
| 11,766,321 B2 * | 9/2023 | Limem | A61F 2/0077 623/8 |
| 2006/0184100 A1 | 8/2006 | Studin | |
| 2014/0343580 A1 | 11/2014 | Priewe | |
| 2015/0032208 A1 | 1/2015 | Preissman | |
| 2019/0099261 A1 * | 4/2019 | Weinzweig | A61B 46/13 |
| 2019/0107250 A1 * | 4/2019 | Rosenberg | F16N 7/12 |
| 2020/0008923 A1 * | 1/2020 | Geiger | A61B 17/3431 |
| 2021/0205069 A1 * | 7/2021 | Gryskiewicz | A61F 2/12 |

* cited by examiner

*Primary Examiner* — Suzette J Gherbi
(74) *Attorney, Agent, or Firm* — Collard & Roe, P.C.

(57) ABSTRACT

A device for inserting a pre-filled or silicone prosthesis into a surgical pocket is formed from a sleeve formed of a trapezoidal bottom layer and a trapezoidal top layer attached to the bottom layer along longitudinal edges of the bottom layer and top layer. The top layer has a greater width than the bottom layer so as to form a shape of half of a truncated cone or a tapered half cylinder when the sleeve is filled. The sleeve has a constantly decreasing cross-sectional area along a length of the sleeve. This device reduces the chances for the implant to rotate in an unintended manner due to the non-circular cross-section of the sleeve and prevents inadvertent exit of the implant prior to placement in the surgical pocket.

11 Claims, 2 Drawing Sheets

DEVICE FOR DELIVERING SILICONE PROSTHESIS INTO A SURGICAL POCKET

BACKGROUND OF THE INVENTION

1. Field of Invention

This invention is a delivery apparatus which allows the placement of a pre-filled silicone breast prosthesis through a minimal access type of incision without damaging the shell of the implant by force or manipulation. This delivery apparatus prohibits the implant from turning while being placed into the pocket, ending upside down or in any other position that it was not intended to be placed, positioned or remain. The device also prevents inadvertent exit of the implant from the sleeve prior to placement in the surgical pocket.

2. The Prior Art

Silicone implants have been available and in use for over 50 years. They are sold in a pre-filled condition. There are multiple unintended consequences to implant placement without a device or with a device that is ineffective in placement. The surgical placement of the implant without a device necessitates longer incisions, which lead to longer scars, which is not usually preferred by the patient or the surgeon. Hand manipulation of the implant for placement can result in trauma to the shell of the implant, causing micro damage or tears that compromise the integrity of the shell and may lead to later shell and implant breakdown. Using the smaller incisions without a delivery device requires the use of even more force to push the implant into the pocket and may cause even more damage to the implant shell. The implants may enter and remain in an upside down position, unknown to the surgeon or patient.

A conical device for delivery of the implant is disclosed in US Patent Application Publication No. 2015/0032208 to Preissman. This device is a conical device with a much larger opening and a smaller delivery port which has to be cut according to the size of the implant being used. However, this device is not without its problems. Since the device does not have a mechanism to keep the implant oriented as it is being placed, the implant has a tendency to rotate as it is being delivered. It is not always possible to see this, even though the device is transparent. Therefore, the implant may end up in the patient in an unintended position. For example, the implant may be delivered upside-down. Repositioning the implant within the pocket can create the same surgical trauma to the shell that the device was attempting to avoid. Likewise, the process of removing the implant from the pocket in order to replace it again in the proper orientation using the device can result in the same kind of trauma to the shell.

Therefore, there is room for improvement of the shape of the device that is used to place the implant in the pocket. This new device reduces the chances for the implant to rotate in a non-intended manner, such as being delivered upside-down, or in any other position in which the implant was not meant to be delivered, oriented, deposited or permanently left in the patient.

U.S. Pat. No. 11,035,151 to Bakshandeh addresses some of these issues, by providing an implant delivery device that is in the shape of half-cylinder. The flat side of the device keeps the implant in the proper orientation during delivery so that it does not rotate. However, there is the rise that the implant could slide out of the delivery end prior to implantation, due to the constant cross-sectional size of the device. Therefore, it would be desirable to provide a device that prevents rotation of the implant and prevents inadvertent exit of the implant during use as well as allows the implant to be delivered through a smaller incision with no microtrauma to the implant shell.

SUMMARY OF INVENTION

The present invention relates to an implant delivery device that consists of a rounded top portion and a flat bottom portion. The device is an implant delivery device that is a half-circle in cross-section and takes the form of a tapered half cylinder or half of a truncated cone, so that the cross-section of the device decreases along its length, proximally to distally, with (distal being the patient-facing end). The device is formed from two trapezoidal pieces of pliable film that differ in width but have the same length. The trapezoidal top portion segment of the device is wider along the entire length than the trapezoidal piece which forms the bottom portion of the device so that when assembled the device is in the form of half of a truncated cone or a tapering half cylinder, having one flat side and an opposite side in the shape of a truncated cone or tapered half cylinder. The device thus forms a tapered sleeve where the cross-sectional area of the device decreases throughout its length. The breast prosthesis is introduced through the larger end and propelled through the device with hand pressure through the opposite end, underneath the breast or chest muscle, into the surgically created cavity. The device according to the invention is used for the placement of the silicone prosthesis into the pocket through a minimal access/much smaller incision that would necessarily need to be created to place this kind of prosthesis. For larger implants, the device can be trimmed at the distal end to create a larger opening to allow the implant to pass through.

When using the device according to the invention, the flat bottom portion of the device is oriented and parallel to the flat base of the implant. The implant is placed within the empty lumen of the device. With the implant already within the device in its proper orientation, the device is placed within the minimal access incision with its flat base facing down, which is also parallel to the patient in a supine position. The implant, therefore, is now also oriented in its proper orientation which is with the flat base of the implant on the posterior flat portion of the device. This flat bottom portion of the device is parallel to the chest wall. The opposite concave surface of the implant, which is oriented and abutting the concave interior surface of the upper portion of the device, which is now facing and on the breast or muscle side of the surgical pocket. In this manner of depositing the implant with the device according to the invention, the pocket and implant are all in a coordinated parallel orientation and the implant has less of a chance of rotating during the process and secondary malposition with the need for repositioning.

The device holds the implant it its lumen and prevents inadvertent rotation, malposition or mal-placement of the implant.

The length of both pieces used to make the device are exactly the same—only the width of the pieces are different and are held together with seams along both longitudinal edges, which converge from one end to the other. In one embodiment, the flat bottom portion of the device may be made of a more rigid substance so that it maintains its flat shape during use. The concave top portion is made of a similar material that is more pliant, so that it can stretch to accommodate the implant as it is being propelled through the device. The concave top portion is attached and looks like a dome in cross-section, with both edges/sides attached to the flat base along the seams. The top piece forming the top portion is wider, so it will form pleats when it is folded flat and when it is attached to the sides of the narrower flat base. The attachment can be by any method including heat sealing or other means. The material of the top portion is pliant so that it is perfectly flat when the implant is not within its lumen/pocket so that it can be packaged and shipped as a flat parcel.

The device can be made of any product including plastic, silicone or other material. Preferably, the device is transparent, but it can also be made of non-transparent materials. Possible choices of materials include MYLAR® RTM (bi-axially-oriented polyethylene terephthalate), TYGON® RTM and different compositions of ethylene and alpha-olefin copolymers which are used to make intravenous bags that hold fluids. The device can be made in various diameters, half diameters or sizes. These sizes will vary according to the size of the breast implant or other object that needs to be transported from the outside to a surgically created cavity inside a patient underneath the breast. The degree of narrowing from one end to the other can also vary, as long as the prosthesis can be pushed through the smaller opening in the device and into the surgical pocket.

The material in the flat bottom portion may be a little thicker and less pliable than the roof section. The material forming the top portion may be a little more pliant and stretch with applied internal pressure and force. This is intended mainly for the use of placing a breast implant within the surgically created pocket through a smaller incision without damaging the shell of the implant with minimal trauma to the shell of the implant. The distal end of the device has a cross-section that is generally smaller than the cross-section of the implant, so that the implant must be squeezed through the distal end under pressure. This ensures that the implant will not inadvertently slide out of the device prior to intended placement in the breast cavity.

All breast implants have a front and a back surface. The front of the implant is convex and the back is usually flat or flatter. The breast implant will be placed in the device in its anatomically proper position. The top of the implant will be facing up and the bottom of the implant, which is flat, will be facing the flat bottom portion of the half cylinder. The device will envelop the implant, keeping the implant in its anatomically correct position, preventing the implant from rotating during placement and being introduced in the manner that the implant was not intended to be placed in the cavity.

The device may be coated with a lubricating type of coating that will be activated with the introduction of any kind of liquid substance. This lubricating material will allow the implant to slide through the device without any friction. The lubricating material can be made of any water soluble lubricant such as K-Y® jelly, which is a water-soluble lubricant containing glycerol and hydroxyethylcellulose. The lubricant can be mixed with a combination of 4% chlorhexidine, a surgical skin preparatory solution used for its ability to reduce or eradicate skin pathogens and BETA-DINE®, an iodine based solution which is also bactericidal. This combination of substances will coat the implant and allow it to be propelled through the device into the breast pocket. The combination of the 4% Chlorhexidine and BETADINE® will also coat the implant as it is being placed into the pocket with a bactericidal/bacteriostatic layer of protection. This is believed to reduce the incidence of problems such as capsular contracture that may be encountered with breast implants after implantation, although the incidence of capsular contracture is relatively small. The lubricants in the device are dry and they are activated in the operative field with a sterile liquid solution. The implant is then placed within the device. One end of the device is placed through the incision into the surgically prepared cavity. The implant is then propelled through the device and into the cavity with the application of pressure to the device which is transferred to the implant. Alternatively, the material used to manufacture the device may have the lubricant already applied or disposed within the material. The implant may be made and transported with the lubricants in a liquid or other form as well.

The device is made of materials that can be sterilized before use. Common methods of sterilization include gas and heat sterilization.

As previously mentioned, the device can be made in many sizes to accommodate the many sizes of implants that are available. However, this can just as easily be accomplished with the availability of three sizes, small, medium and large, or one size only. The smaller device will be used to accommodate the smaller implants, the medium device for the medium range implants and the larger device for the large implants. When using a single size, the device be cut to different sizes by trimming the distal end.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DESCRIPTION OF THE PREFERRED EMBODIMENTS

Figure 1:
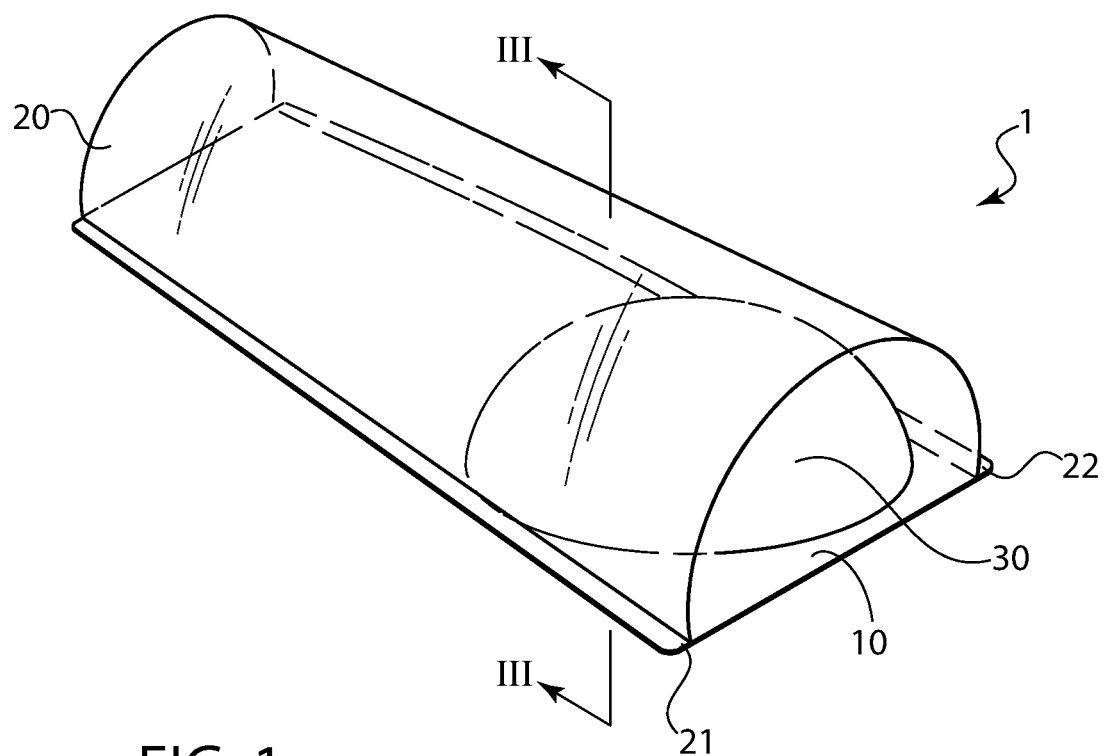
FIG. 1 shows a perspective view of the device according to the invention.
Figure 2:
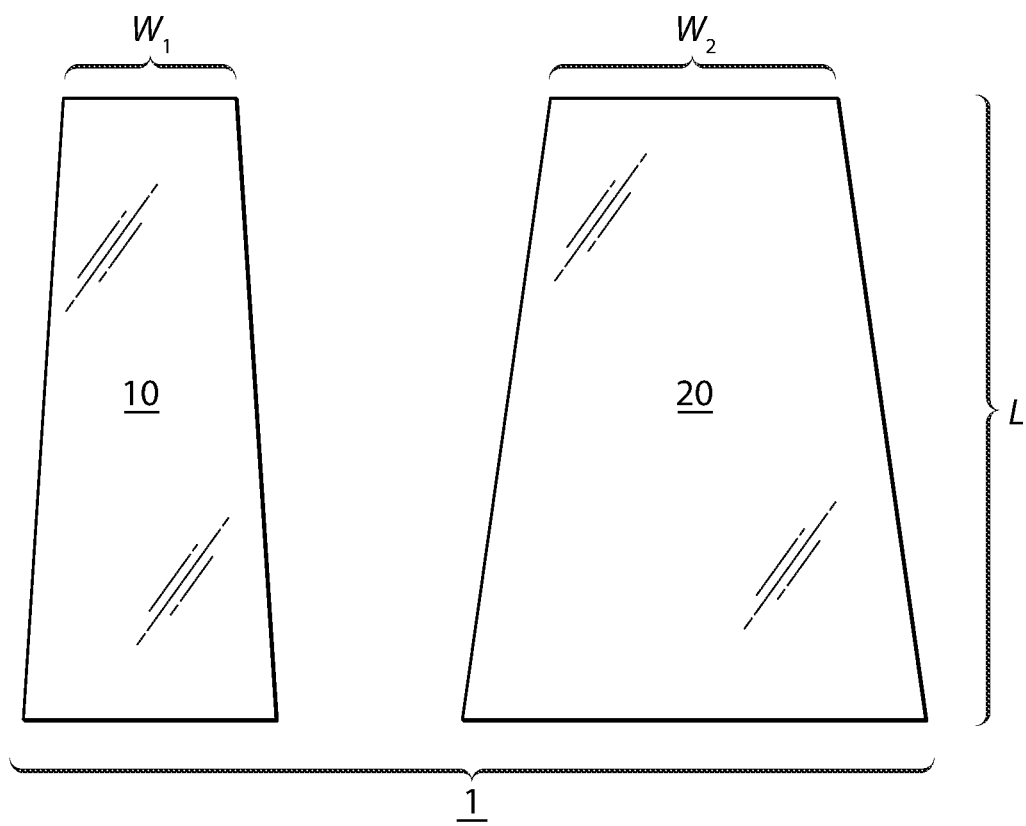
FIG. 2 shows the device in two separate pieces prior to assembly.

FIG. 1 shows the device 1 according to the invention. Device 1 is in the form of a sleeve having a trapezoidal flat bottom portion 10 and a trapezoidal top portion 20, which is connected to bottom portion 10 via two seams 21, 22. An implant 30 can be placed inside the lumen of the device 1, as shown. As can be seen in FIG. 2, the bottom portion 10 is formed of a trapezoid having the same length L as the top portion 10 which is also a trapezoid, but a smaller width $W_1$ than the width $W_2$ of top portion 20.

Device 1 is preferably constructed of a transparent film material that is pliable. Top portion 20 can be made of a different material than bottom portion 10. Top portion 20 is preferably made of a stretchable material. Bottom portion 10 can be made thicker and less pliable for enhanced stability.

Top portion 20 is connected to bottom portion 10 via seams 21, 22, which can be formed by heat sealing or any other suitable method.

Figure 3:
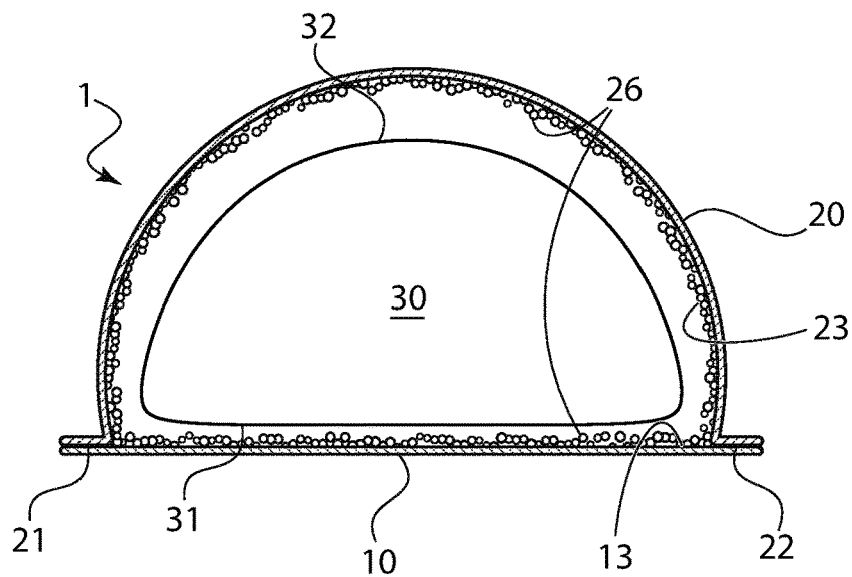
FIG. 3 shows a cross-section of the device along lines 3-3 of FIG. 1, with an implant inserted into the device.

As shown in FIG. 3, an implant 30 can be placed inside device 1, so that the bottom surface 31 of implant 30 rests against bottom portion 10 of device 1. The top surface 32 then conforms to the shape of top portion 20. When the device is expanded, the cross sectional view is that of a half circle. The device when filled takes the shape of a half of a truncated cone or tapered half cylinder, with a flat bottom and a distal end that has a smaller opening than the opening at the proximal end.

A lubricant 26 can be disposed on the inside surface 13 and 23 of top and bottom portions 10, 20, to facilitate movement of prosthesis 30 through device 1. Lubricant 26 can be any suitable lubricant, such as K-Y® jelly, which is a water-soluble lubricant containing glycerol and hydroxyethylcellulose. The lubricant can be mixed with a combination of 4% chlorhexidine, a surgical skin preparatory solution used for its ability to reduce or eradicate skin pathogens and BETADINE®, an iodine based solution which is also bactericidal. This combination of substances will coat the prosthesis 30 and allow it to be propelled through the device into the breast pocket as shown in FIG. 5.

Figure 4:
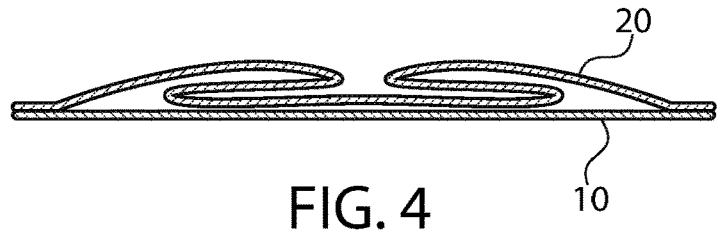
FIG. 4 shows the device in an empty state in a folded position for transport.

When not in use or during transport, device 1 can be folded flat as shown in FIG. 4. Here, the top portion 20 is pleated so as to lie flat against bottom portion 10. This allows many devices 1 to be shipped and stored with a minimum of space.

Figure 5:
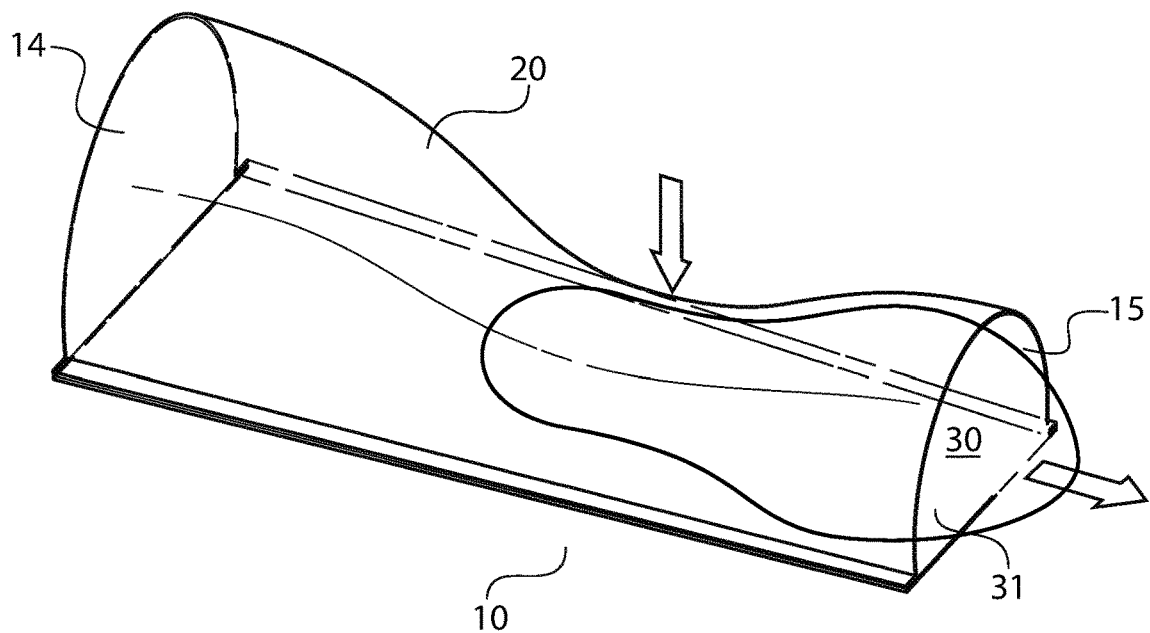
FIG. 5 shows a side view of the device in use for insertion of an implant.

The device in use is shown in FIG. 5. To insert an implant into a surgical pocket, the implant 30 is placed inside device 1 through larger end 14 so that bottom surface 31 of the implant is adjacent bottom portion 10 of the device. The device 1 is then squeezed so that the implant is moved along the sleeve until it exits out smaller end 15 and is delivered into the surgical pocket (not shown). In use, the surgeon generally uses both hands to squeeze device 1 and propel implant 30 through the interior of device 1 into the pocket, and through end 15 under pressure, as the implant 30 in a resting state has a larger diameter than end 15, so must be deformed to fit through end 15. The implant 30 is lodged within the device 1 in its proper orientation and in the manner in which it needs to be deposited without any rotation or turning. The flat and more rigid lower portion of the device keeps the implant from rotating and maintains its orientation during delivery. As shown in FIG. 5, implant 30 exits the device 1 in its proper orientation with the flat base posteriorly and the concave top superiorly in its proper anatomic orientation. The smaller end 15 keeps implant 30 from inadvertently falling out of the device 1 before implantation in the surgical pocket.

Accordingly, while only a single embodiment of the device has been shown and described, many modifications may be made thereunto without departing from the spirit and scope of the claimed invention.

What is claimed is:

1. A device for inserting a pre-filled or silicone implant into a surgical pocket, comprising a sleeve formed of a bottom layer having a proximal end and distal end, two longitudinal edges extending between the proximal end and distal end, with the bottom layer having a decreasing width from the proximal end to the distal end, and a top layer having two longitudinal edges, a proximal end and a distal end, the top layer having a decreasing width from the proximal end to the distal end, wherein the top layer is attached to the bottom layer by seams along the extent of both longitudinal edges of the bottom layer and top layer with a space between the bottom layer and top layer for receiving the implant, wherein the top layer has a greater width between the seams along the entire length of the device than the bottom layer so that the device has a shape of a half of a truncated cone or half of a tapered cylinder, with the bottom layer being flat and the top layer being curved, and wherein the sleeve has a constantly decreasing cross-sectional diameter along a length of the sleeve from the proximal end to the distal end.

2. The device according to claim 1, wherein the bottom layer is formed of a different material than the top layer.

3. The device according to claim 2, wherein the bottom layer is formed of a material having a greater stiffness than the material of the top layer.

4. The device according to claim 1, wherein the top layer is foldable in an unfilled state so as to lie flat with the bottom layer.

5. The device according to claim 1, wherein the device is made of a transparent material.

6. The device according to claim 1, wherein the top layer is made of a stretchable material.

7. The device according to claim 1, wherein an interior surface of the sleeve is coated with a lubricant.

8. A method for inserting a pre-filled or silicone implant into a surgical pocket, comprising:
   providing a sleeve formed of a bottom layer having a proximal end and distal end, two longitudinal edges extending between the proximal end and distal end, with the bottom layer having a decreasing width from the proximal end to the distal end, and a top layer having two longitudinal edges, a proximal end and a distal end, the top layer having a decreasing width from the proximal end to the distal end, wherein the top layer is attached to the bottom layer by seams along the extent of both longitudinal edges of the bottom layer and top layer with a space between the bottom layer and top layer for receiving the implant, wherein the top layer has a greater width between the seams along the entire length of the device than the bottom layer so that the device has a shape of a half of a truncated cone or half of a tapered cylinder, with the bottom layer being flat and the top layer being curved, wherein the sleeve has a constantly decreasing cross-sectional diameter along a length of the sleeve from the proximal end to the distal end, wherein an opening width at the distal end is smaller than a smallest diameter of the implant;
   placing the implant in the sleeve, and
   inserting the implant into the surgical pocket by squeezing the sleeve until the implant exits out of the distal end of the sleeve and into the pocket.

9. The method according to claim 8, wherein the implant has a substantially flat bottom and wherein the step of placing comprises placing the implant in the sleeve so that the substantially flat bottom of the prosthesis abuts the bottom layer of the sleeve.

10. The method according to claim 9, further comprising the step of applying a lubricant to an inside surface of the sleeve.

11. The method according to claim 9, further comprising the step of forming the sleeve by attaching the top layer to the bottom layer by heat sealing.

* * * * *